United States Patent
Ikhlef et al.

(10) Patent No.: US 8,548,119 B2
(45) Date of Patent: Oct. 1, 2013

(54) MULTI-SLICE CT DETECTOR WITH TILEABLE PACKAGING STRUCTURE

(75) Inventors: Abdelaziz Ikhlef, Hartland, WI (US); Brian Joseph Graves, Waukesha, WI (US); Gregory S. Zeman, Waukesha, WI (US); Joseph James Lacey, Cambridge, WI (US); Mayank Gupta, Brookfield, WI (US); Baiju Zacharia Babu, Waukesha, WI (US); Ross Hoggatt, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 331 days.

(21) Appl. No.: 13/005,671

(22) Filed: Jan. 13, 2011

(65) Prior Publication Data

US 2012/0183119 A1    Jul. 19, 2012

(51) Int. Cl.
*H05G 1/60*    (2006.01)
(52) U.S. Cl.
USPC ............................................................ 378/19
(58) Field of Classification Search
USPC ............... 378/19; 250/336.1, 370.11, 370.09
See application file for complete search history.

(56) References Cited

U.S. PATENT DOCUMENTS

| | | | |
|---|---|---|---|
| 6,510,195 B1 * | 1/2003 | Chappo et al. | 378/19 |
| 6,584,167 B1 | 6/2003 | Ikhlef et al. | |
| 6,979,826 B2 | 12/2005 | Ikhlef | |
| 7,149,284 B2 | 12/2006 | Ikhlef | |
| 7,233,640 B2 | 6/2007 | Ikhlef et al. | |
| 7,399,119 B2 | 7/2008 | Chao et al. | |
| 7,455,454 B2 | 11/2008 | Ikhlef et al. | |
| 7,602,951 B2 | 10/2009 | Hsieh et al. | |
| 7,620,143 B2 | 11/2009 | Ikhlef et al. | |

* cited by examiner

*Primary Examiner* — Jurie Yun
(74) *Attorney, Agent, or Firm* — Ziolkowski Patent Solutions Group, SC

(57) ABSTRACT

A CT system is disclosed that includes detector modules positioned on a rotatable gantry configured to receive x-rays attenuated by an object. Each detector module includes a module frame, a plurality of tileable sub-modules on the module frame aligned along a Z-axis thereof to receive the x-rays attenuated by the object and convert the x-rays to digital signals, and an electronics board connected to the plurality of sub-modules to receive the digital signals. Each sub-module further includes an array of detector elements to receive x-rays attenuated through the object and convert the x-rays into analog electrical signals, an ASIC electronics package coupled to the array of detector elements to receive the analog electrical signals and convert the analog electrical signals to digital signals, and a flex circuit connected to the ASIC electronics package to receive the digital signals and transfer the digital signals to the electronics board.

22 Claims, 8 Drawing Sheets

ANALOG SIDE

MULTI-SLICE CT DETECTOR WITH TILEABLE PACKAGING STRUCTURE

BACKGROUND OF THE INVENTION

Embodiments of the invention relate generally to radiographic detectors for diagnostic imaging and, more particularly, to a Computed Tomography (CT) detector module having a plurality of tileable sub-modules that provide for increased slice acquisition and improved detector performance.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are sent to the analog-to-digital convertors and then sent for processing into digital images.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector and rejecting scatter from the patient, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In the last decade, the development of volumetric or cone-beam CT (VCT) technology has led to a rapid increase in the number of slices (Z-axis) used in CT detectors. Indeed, the detectors used in VCT are enabling more and more coverage in patient scanning by increasing the patient area exposed. In order to accommodate such coverage, the width of CT detectors has been increased in the Z-axis (i.e., direction of patient length). The x-ray detectors of current state of the art CT systems are composed of a 2D array of scintillating pixels, coupled to a 2D array of silicon photodiodes, with the typical array being sized so as to be capable of providing for acquisition of various different slice types (e.g., 16, 32, or 64 slices), with an array size of 40 mm at ISO for a 64 slice configuration.

Recently, however, the need for cardiac imaging has become more and more of interest and imaging of the heart within one rotation has become a requirement. In order to image the heart in one rotation, the detector array size needs to be ~160 mm at ISO to cover the full organ in half scan, which is equivalent to a detector capable of capturing heart anatomy in one motion (e.g., 256 slices in our case). However, increasing the coverage of the detector in the Z-axis beyond 64 slices up to 256 slices can be problematic. For example, a long scintillating array and long photodiode array can be used to increase the coverage of the detector in the Z-axis beyond 64 slices; however, the use of such long scintillating and long photodiode arrays presents a challenge regarding manufacturability for reasons such as yield, cost, testability, dimensional accuracies, and performance.

Therefore, it would be desirable to design a CT detector that provides for VCT cardiac imaging by accommodating data acquisition of sufficient coverage and pixilation to provide detailed anatomic structure of the heart within a single rotation. It would also be desirable for such a CT detector to have a tile-able construction that enables ease of manufacturing, scalability, early testability, serviceability, and performance optimization of the detector.

BRIEF DESCRIPTION OF THE INVENTION

The invention is a directed apparatus for CT image acquisition that provides for increased slice acquisition with improved detector performance.

In accordance with one aspect of the invention, a CT system includes a rotatable gantry having an opening to receive an object to be scanned, an x-ray projection source positioned on the rotatable gantry that projects a cone beam of x-rays from a focal spot of the x-ray projection source toward the object, and a plurality of detector modules positioned on the rotatable gantry and configured to receive x-rays attenuated by the object. Each of the plurality of detector modules includes a module frame having a top surface thereon, a plurality of tileable sub-modules positioned on the top surface of the module frame and aligned along a Z-axis thereof so as to receive the x-rays attenuated by the object and convert the x-rays to digital signals, and an electronics board connected to the plurality of sub-modules to receive the digital signals therefrom. Each of the plurality of sub-modules on the detector module further includes an array of detector elements configured to receive x-rays attenuated through the object and convert the x-rays into analog electrical signals, an application specific integrated circuit (ASIC) electronics package electrically and mechanically coupled to the array of detector elements to receive the analog electrical signals and convert the analog electrical signals to digital signals, and a flex circuit connected to the ASIC electronics package to receive the digital signals therefrom and transfer the digital signals to the electronics board of the detector module.

In accordance with another aspect of the invention, a detector module for receiving x-rays attenuated by an object during a CT scan procedure includes a module frame, a plurality of tileable sub-modules positioned on the module frame to receive the x-rays attenuated by the object, and an electronics processing board secured to the module frame and electrically connected to the plurality of sub-modules to process signals received therefrom. Each of the plurality of sub-modules further includes an array of detector pixels configured to receive x-rays attenuated through the object and convert the x-rays into analog electrical signals, an application specific integrated circuit (ASIC) electronics package electrically and mechanically coupled to the array of detector pixels to receive the analog electrical signals and convert the analog electrical signals to digital numbers, and a digital flex circuit connected to the ASIC electronics package to receive the digital numbers therefrom and transfer the digital numbers to the electronics board of the detector module.

In accordance with yet another aspect of the invention, a detector module for receiving x-rays attenuated by an object during a CT scan procedure includes a module frame, a plurality of selectively addable sub-modules positioned on the module frame to receive the x-rays attenuated by the object, and an electronics processing board secured to the module frame and electrically connected to the plurality of sub-modules to process signals received therefrom. Each of the plurality of sub-modules includes a scintillator array having a plurality of scintillator pixels configured to receive x-rays attenuated through the object and generate a light output responsive thereto and a photodiode array optically coupled to the scintillator array and comprising a plurality of photodiodes each configured to detect the light output from the scintillator array and generate the analog electrical signals responsive thereto. Each of the plurality of sub-modules further includes an analog-to-digital (A/D) converter electrically and mechanically coupled to the array of detector elements to receive the analog electrical signals and convert the analog electrical signals to digital numbers, a substrate layer positioned on a back surface of the A/D converter opposite from the photodiode array to provide support to the sub-module, and a digital flex circuit connected to the A/D converter to receive the digital numbers therefrom and transfer the digital numbers to the electronics board of the detector module, the digital flex circuit including an interface portion thereon positioned between the A/D converter and the substrate layer to form an electrical and mechanical coupling with the A/D converter.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a 256 slice computed tomography (CT) system. However, as will be explained in detail below, the invention is equally applicable for use with other multi-slice configurations between sixty-four slices and 256 slices, and beyond, such as up to 512 slices. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
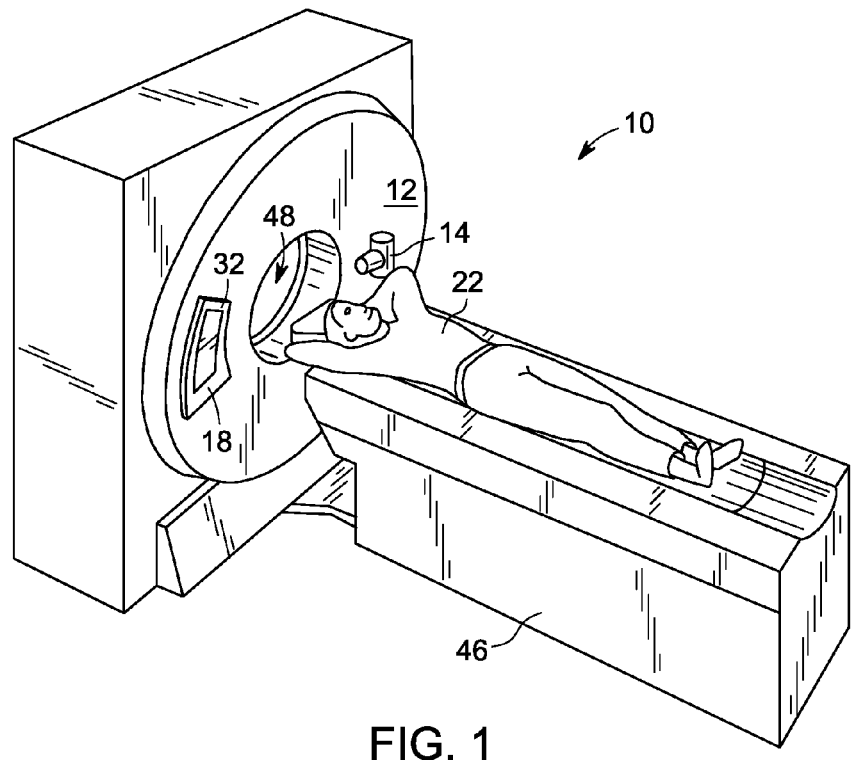
FIG. 1 is a pictorial view of a CT imaging system.
Figure 2:
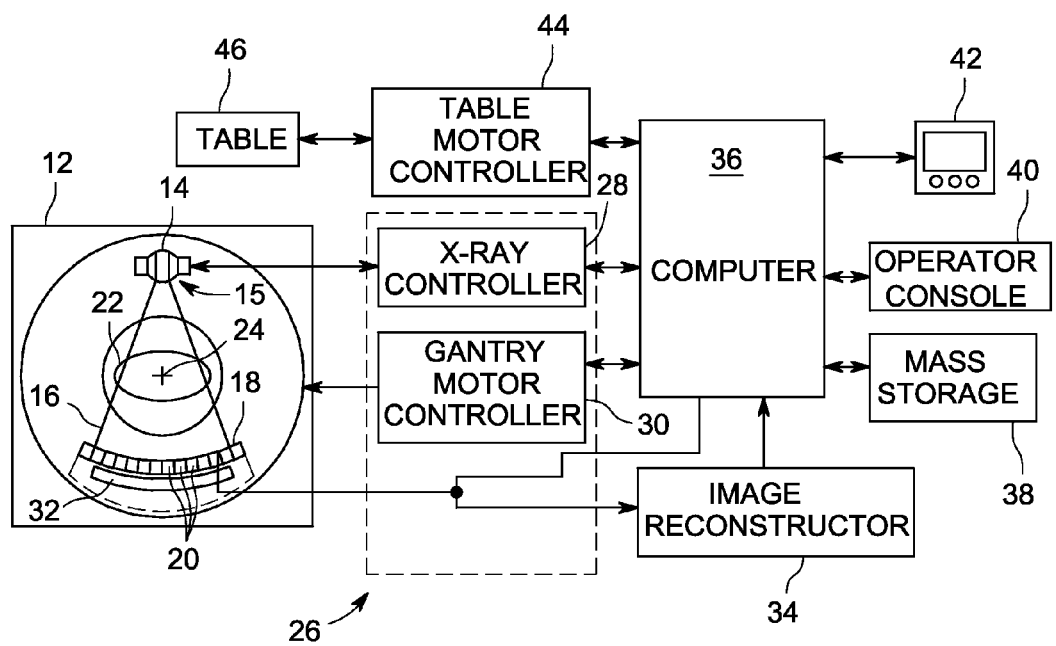
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays from a focal spot 15 of the source 14 and toward a detector assembly 18 on the opposite side of the gantry 12. Referring now to FIG. 2, detector assembly 18 is formed by a plurality of detector modules 20 and a control and processing board 32 (i.e., electronics board). The plurality of detector modules 20 sense the projected x-rays 16 that pass through a medical patient 22, with the electronics board 32 performing subsequent processing on the acquired data. Each detector module 20 produces an output that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from electronics board 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to electronics board 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
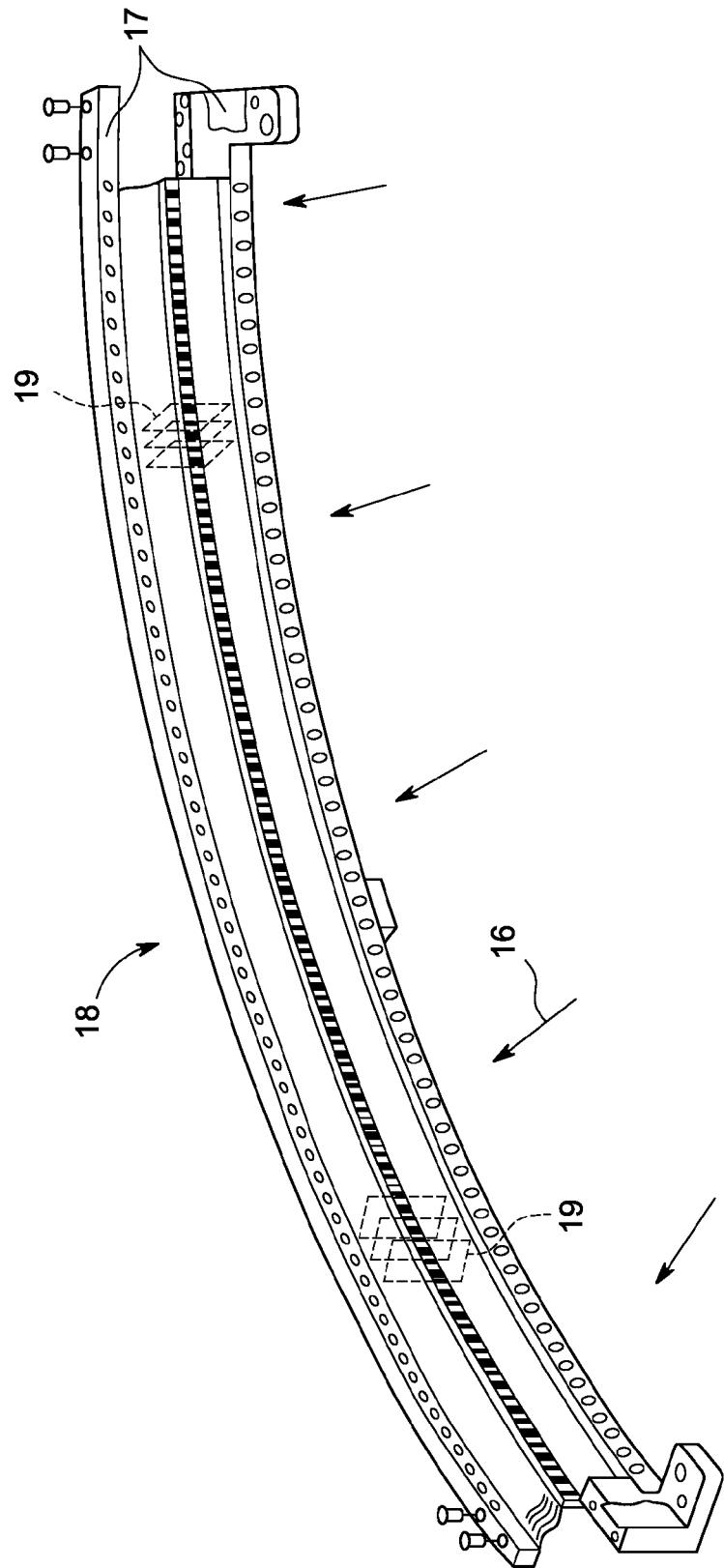
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector module 20 of FIG. 4 positioned on detector assembly 18. According to an embodiment of the invention, detector assembly 18 includes 57 detector modules 20, each detector module 20 having an array size of 256×16 of pixel elements, as will be explained in detail below. As a result, detector assembly 18 has 256 rows and 912 columns (16×57 detectors), which allows 256 simultaneous slices of data to be collected with each rotation of gantry 12. However, while an exemplary detector module 20 is set forth as having an array size of 256×16 of pixel elements, it is recognized that the number of rows and columns in detector assembly 18 can be selectively controlled based on the structure of detector modules 20 according to embodiments of the invention, such that the number of slices simultaneously collected can be lesser or greater in number, such as up to 512 slices of data.

Figure 4:
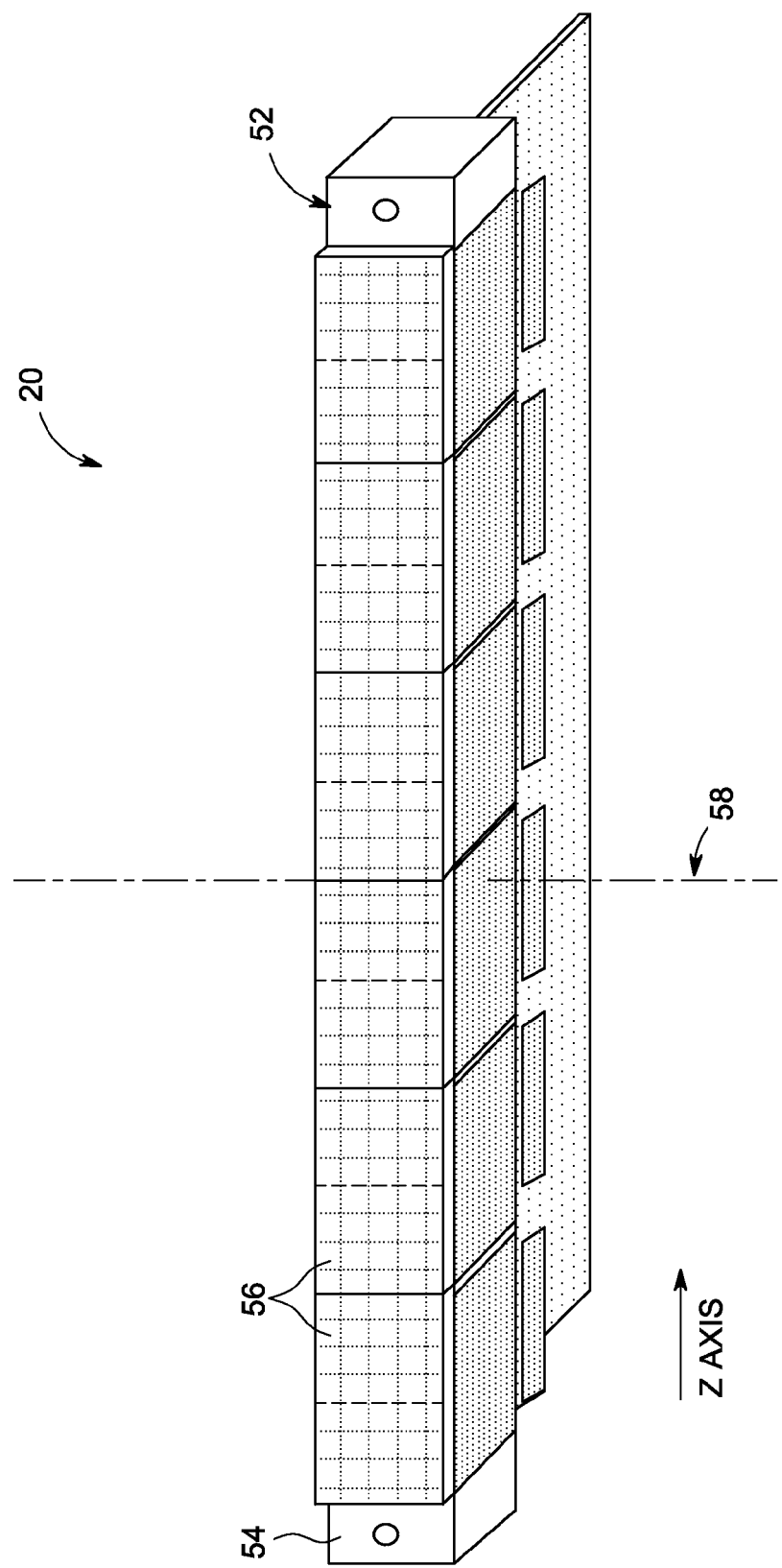
FIG. 4 is a perspective view of a detector module according to an embodiment of the invention.

Referring to FIG. 4, construction of a detector module 20 is shown according to an exemplary embodiment of the invention. The detector module 20 includes a module frame 52 having a top surface 54 thereon. According to embodiments of the invention, top surface 54 can be constructed as a flat surface, an approximated curve formed in a circular arc not following the arc of the x-ray beam, or a stepped configuration with a plurality of angled facets thereon, as will be explained in detail below. As shown in FIG. 4, a plurality of detector sub-modules or "nano-modules" 56 are positioned onto top surface of module frame 52 and aligned along the Z-axis to receive and process x-rays that attenuate through a patient or object. According to embodiments of the invention, the number of sub-modules 56 positioned on top surface 54 of module frame 52 can be controlled during a manufacturing process based on the operating requirements of detector modules 20 in the CT system 10 (FIG. 1). That is, the sub-modules 56 of detector module 20 are configured as tileable sub-modules, in that sub-modules 56 can be selectively added to module frame 52 as desired such that the number of sub-modules 56 included in detector module 20 can be controlled, so as to vary the amount of coverage along the Z-axis (i.e., vary/control the number of slices acquired). Thus, for example, according to one embodiment of the invention, six sub-modules 56 may be included in detector module 20. However, other embodiments of detector module 20 could include four, eight, or twelve sub-modules 56, for example, as indicated by the phantom lines shown in FIG. 4. In each embodiment, the sub-modules 56 are positioned on top surface 54 in a symmetrical fashion about a centerline 58 of the detector module along the Z-axis. Thus, based on a populating and depopulating of sub-modules 56 on module frame 52, it is recognized that a detector module 20 can be built having a controllable length/coverage along the Z-axis.

Figure 5:
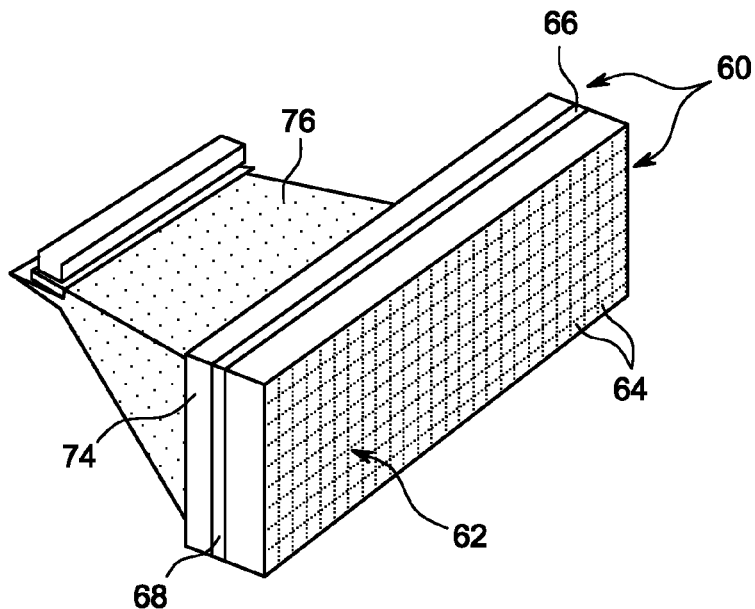
FIGS. 5 and 6 are views of a detector sub-module for use with the detector module of FIG. 4 according to an embodiment of the invention.
Figure 6:
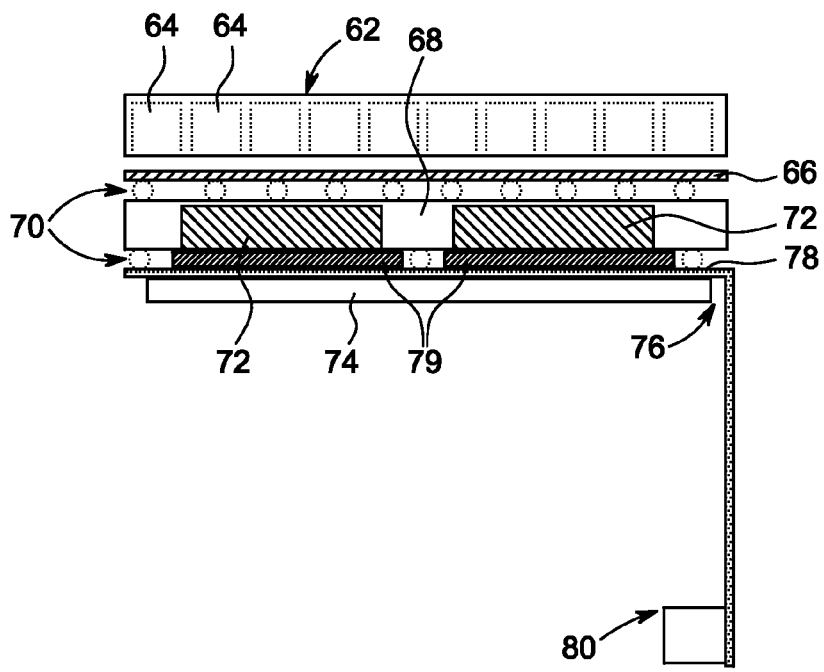

A detailed view of a sub-module 56 is shown in FIGS. 5 and 6 according to an embodiment of the invention. Sub-module 56 includes an array of detector elements or pixels 60 that are configured to receive x-rays attenuated through the object and convert the x-rays into analog electrical signals. According to one embodiment, the detector elements/pixels 60 are formed from a scintillator-photodiode pair. In forming the scintillator-photodiode pair, a number of scintillator detector elements or pixels 62 are arranged to form a scintillating pack array 64. For example, a scintillating pack array 64 may be composed of a 32×16 array of scintillator detector elements 62, such that each scintillating pack array 64 includes 32 slices. The scintillating pack array 64 is positioned on a photodiode array 66 formed of a plurality of diode elements or pixels (not shown), with the diode array 66 being formed of a 32×16 array of diodes, for example, that corresponds to the number of scintillator detector elements 62.

As shown in FIGS. 5 and 6, scintillator detector elements 62 are optically coupled to diode array 66 and diode array 66 is in turn electrically coupled to one or more application specific integrated circuit (ASIC) electronics packages 68. The ASIC electronics package 68 (i.e., analog-to-digital (A/D) convertor) is electrically and mechanically coupled to diode array 66 by way of an input/output (I/O) interconnect 70 formed thereon (i.e., on front and back surfaces of the ASIC electronics package 68). The I/O interconnect 70 may be formed as a ball grid array (BGA) type interconnect, for example, or another similar bonding device that electrically and mechanically couples the ASIC electronics package 68 to diode array 66. According to embodiments of the invention, each ASIC electronics package 68 includes one or more individual ASIC dies 72, such as four ASIC dies 72, that collectively form the package 68.

According to embodiments of the invention, ASIC electronics package(s) 68 is configured, in part, to perform analog-to-digital (A/D) conversion of signals received from photodiode array 66. That is, ASIC electronics package 68 functions to convert analog electrical signals received from photodiode array 66 into digital numbers based on a level of the signal received from the diode array. Thus, in the operation of one embodiment, x-rays impinge within scintillator detector elements 62 to generate photons that traverse pack array 64 and are detected on a photodiode pixel/element within diode array 66, with an analog signal generated by diode array 66 responsive thereto being received by ASIC electronics package(s) 68 for conversion to a digital signal/number.

As further shown in FIGS. 5 and 6, a substrate layer 74 (i.e., ASIC package substrate) is positioned beneath ASIC electronics package(s) 68 and opposite from scintillating pack array 64. The substrate layer 74 is formed of an electrically insulating material and is configured to provide support/rigidity to sub-module 56. Positioned between substrate layer 74 and ASIC electronics package(s) 68 is a flex circuit 76 attached to ASIC electronics package 68 that routes signals from the ASIC electronics package to control and processing board 32 of the detector module 20 (FIG. 4), and also transfers controls and power to/from the control and processing board 32. The flex circuit 76 is in the form of a "digital flex circuit" in that it functions to transmit digital signals/numbers from the ASIC electronics package 68. The flex circuit 76 includes a connector/electrically bondable area 78 configured to interface with ASIC electronics packages 68 (i.e., interface with I/O interconnect 70) and a connector 80 configured to interface with control/processing board 32 of the detector module 20 (FIG. 4). According to one embodiment, connector/electrically bondable area 78 of flex circuit 76 has holes formed therein (not shown) that correspond to the ASIC dies in ASIC electronics package 68 to thermally bond the substrate layer 74 (via pedestals) to the ASIC electronics package 68.

Figure 7:
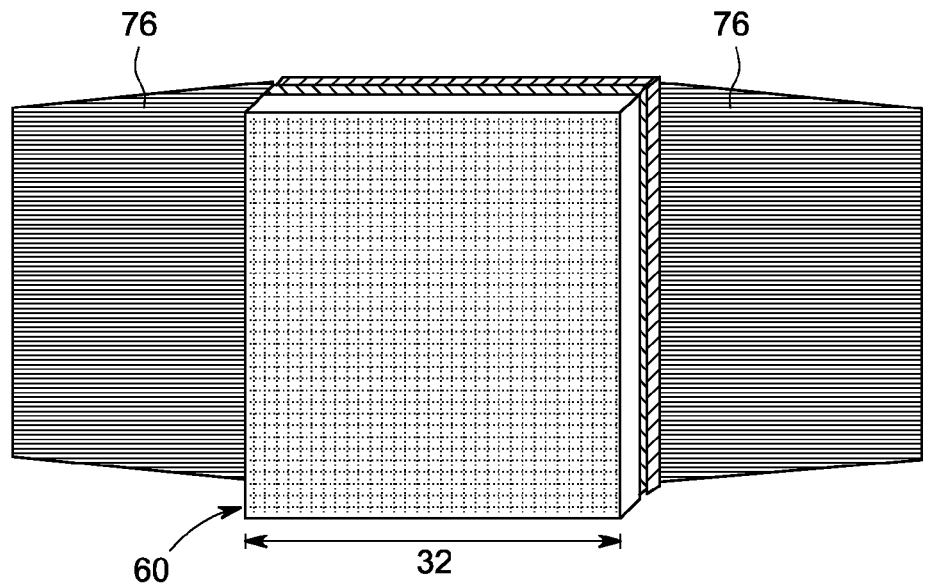
FIG. 7 is a view of a double-sided digital flex circuit of a detector sub-module according to an embodiment of the invention.

Also, according to an embodiment, a thermal adhesive 79 is also provided between ASIC electronics package 68 and flex circuit 76 to bond the components together, as well as provide a separate thermal interface for sub-module 56. While flex circuit 76 is shown in FIGS. 5 and 6 as a single-sided flex circuit, it is recognized that flex circuit 76 could alternatively be constructed as a double-sided flex circuit 76 such as shown in FIG. 7, with a flex circuit extending down each of opposing sides of module frame 52 (FIG. 4). It is further recognized that other interconnect options could equally be used such as ribbon cable or board-to-board connections. Also shown in FIG. 7 is that the array of detector elements/pixels 60 may be formed of a 32×32 array of pixels, such that sub-module 56 may have a square configuration.

Figure 8:
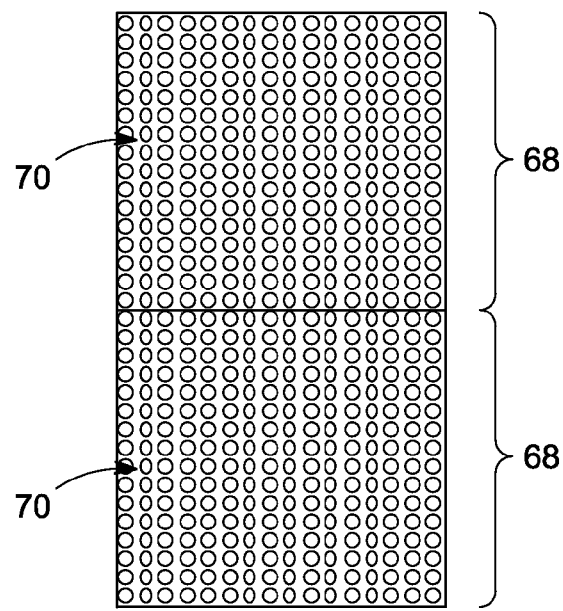
FIGS. 8-10 are views of input-output interconnects for ASIC electronics packages of a detector sub-module according to embodiments of the invention.
Figure 9:
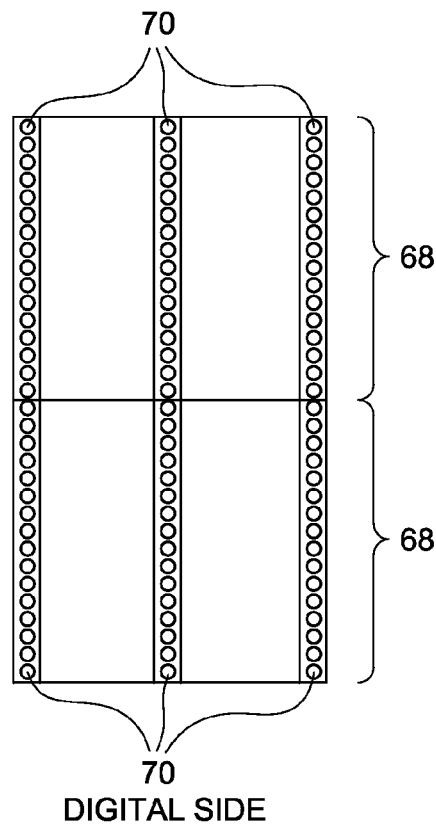
Figure 10:
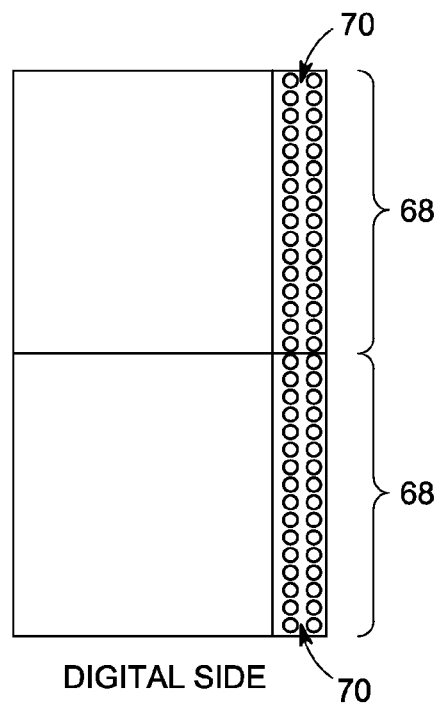

Referring now to FIGS. 8-10, structures of ASIC electronics package 68 and the I/O interconnect 70 thereon are shown according to embodiments of the invention. As shown in FIGS. 8-10, according to one embodiment, two ASIC electronics packages 68 are provided for each sub-module 56. FIG. 8 shows the analog side of ASIC electronics packages 68, with an I/O interconnect 70 that is connected to photodiode array 66 (FIGS. 5-6). FIGS. 9 and 10 show the digital side of ASIC electronics packages 68, according to embodiments of the invention, with FIG. 9 showing an I/O interconnect 70 that is connectable to a double-sided flex circuit 76 (FIG. 7) and FIG. 10 showing an I/O interconnect 70 that is connectable to a one-sided flex circuit 76 (FIGS. 5-6). According to an exemplary embodiment, I/O interconnect 70 is in the form of a ball grid array (BGA) or similar type connection that provides mechanical and electrical coupling between photodiode array and ASIC electronics packages.

As shown in FIGS. 8-10, for each sub-module 56, two ASIC electronics packages 68 are provided to accommodate receiving/processing of analog signals and conversion of those analog signals to digital signals/numbers. According to embodiments of the invention, each ASIC electronics package 68 may include between one and four ASIC dies 72 (FIG. 6), with each ASIC die 72 having 64 analog channels, for example. The ASIC dies 72 may be arranged in an H pattern array, single row linear array, rows vs. columns array, or as a single package. According to an exemplary embodiment of the invention, each sub-module 56 includes two ASIC electronics packages 68, with each ASIC electronics package 68 having four ASIC dies 72 therein, such that a total of eight ASIC dies 72 are provided in each sub-module 56.

Referring again now to FIGS. 5 and 6, it is recognized that coupling of ASIC electronics package 68 directly to the scintillator and photodiode pair 64, 66 beneficially provides decreased electronic noise as compared to traditional analog flex routing and associated interconnects, thereby providing a higher signal-to-noise ratio (SNR). That is, it is recognized that the primary disadvantage of analog signaling is noise—i.e., random unwanted variation. As the signal is copied and re-copied, or transmitted over long distances, such as transmission over an analog flex circuit, these apparently random variations become dominant, thus resulting in electrical noise. In addition, close coupling of the photodiode array to the ASICs (A/D convertors) reduces the power requirements and the corresponding heat that is generated. Thus, conversion of the analog electrical signals generated by photodiode array 66 to digital numbers directly at the ASIC electronics package(s) 68 (i.e., A/D conversion at ASIC electronics packages 68) of sub-module 56 serves to reduce noise and increase SNR, as the need to transmit an analog signal over a longer distance (i.e., over a flex circuit) is eliminated.

In addition to improving the SNR, coupling of ASIC electronics package(s) 68 directly to the scintillator and photodiode pair 64, 66 also provides improved reliability of the detector module 20 by reducing the number of electrical interconnects and components, specifically with respect to the high-density analog flex circuits found in traditional detector modules. The use of ASIC electronics package(s) 68 in sub-module 56 also serves to reduce the cost per unit area (i.e., per pixel) of the overall detector module 20 by reducing the number of components and interfaces included therein.

Further benefits are provided by the structure and inclusion of sub-modules 56 in detector module based on the controllable and variable nature of sub-modules, both with regard to the tileability and sizing of sub-modules. That is, according to embodiments of the invention, the configuration of sub-module 56 can be varied in order to optimize for performance and scalability. That is, while a sub-module 56 is described above as having an array of 32×16 detector pixels/elements (i.e., 32 slices and 16 channels), it is recognized that the sub-module 56 may be formed so as to have any one of a number of N×M arrays of pixels/elements (e.g., N=16, 32, or 64, M=16, 24, or 32, for example), with the size of the array being optimized based on cost, performance, yield, testing time scalability, reliability, etc. Correspondingly, the dimensions of the sub-module 56 may vary, with the sub-module 56 having a length (i.e., dimension along the Z-axis) from 10 mm in length up to 40 mm in length depending on the exact configuration of detector module 20. Furthermore, while sub-module 56 is shown in FIGS. 5 and 6 as including scintillator array 64 and photodiode array 66, it is recognized that such elements/materials in sub-module 56 could be replaced with a direct conversion material that directly converts x-rays into electrical signals, such as cadmium-telluride (CdTe) or cadmium-zinc-telluride (CZT).

Figure 11:
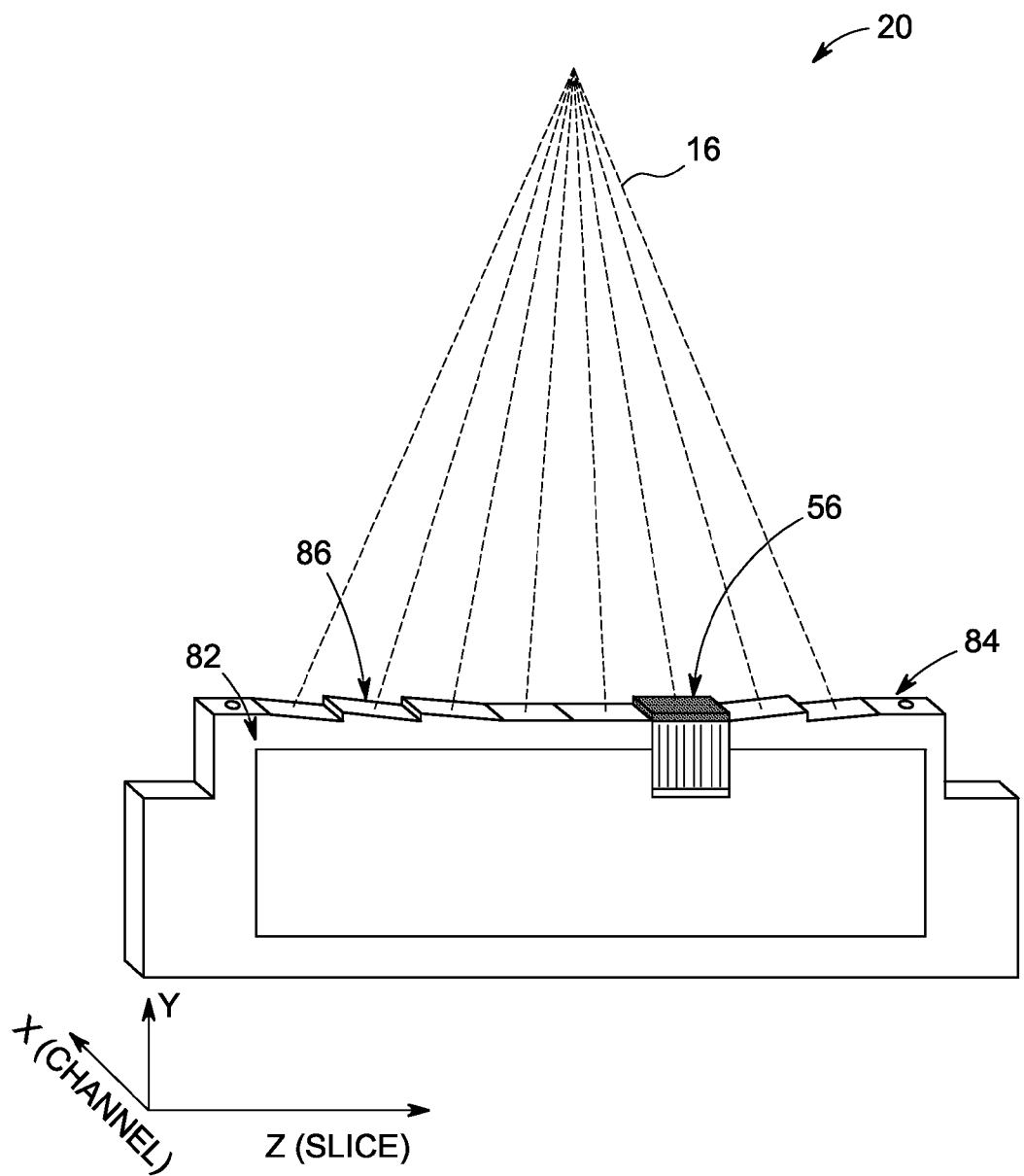
FIG. 11 is a perspective view of a detector module according to an embodiment of the invention.

Referring now to FIG. 11, construction of a detector module 20 is shown according to another embodiment of the invention. The detector module 20 includes a module frame 82 having a top surface 84 constructed to have a stepped configuration and thus includes a plurality of facets 86 thereon. The facets 86 are aligned lengthwise along the module frame 82, along the Z-axis, with each facet 86 being sized and configured to accommodate a detector sub-module 56 to receive and process x-rays that attenuate through a patient or object. According to one embodiment of the invention, eight facets 86 are formed on the top surface 84 of module frame 82, with a sub-module 56 positioned on each facet 86, such that the summation of each 32×16 array of detector elements in each sub-module 56 results in an array size of 256×16 of detector elements for detector module 20. As a result, detector module 20 provides for 256 simultaneous slices of data to be collected with each rotation of gantry 12 (FIG. 1).

As shown in FIG. 11, module frame 82 is configured such that each facet 86 positions a respective sub-module 56 at a certain angle with respect to the x-ray beam focal spot 15 in order to avoid the parallax effect. The angle at which each facet 86 is formed is individually optimized such that the slices of sub-modules 56 are minimally affected by a parallax phenomenon (i.e., minimizes x-ray crosstalk between slices, spectral non-linearity, slice profile degradation, and MTF deterioration), with the angle of each facet 86 with respect to the focal spot 15 being varied/determined as a function of the performance desired and the specific image quality parameter to improve. In general, the angle of a particular facet 86 relative to the focal spot 15 will increase the further the facet 86 is from the centerline 58 of detector module 20. Thus, the outermost facets 86 on module frame 52 may be oriented at a greater angle relative to focal spot 15 than the middle facets 86 on module frame 82 adjacent to the centerline 58. Sub-modules 56 are then positioned on facets 86 and secured thereto so as to be positioned at desired angles formed by their corresponding facet 86, such as via an adhesive, screws, or any other acceptable fastening method.

Figure 12:
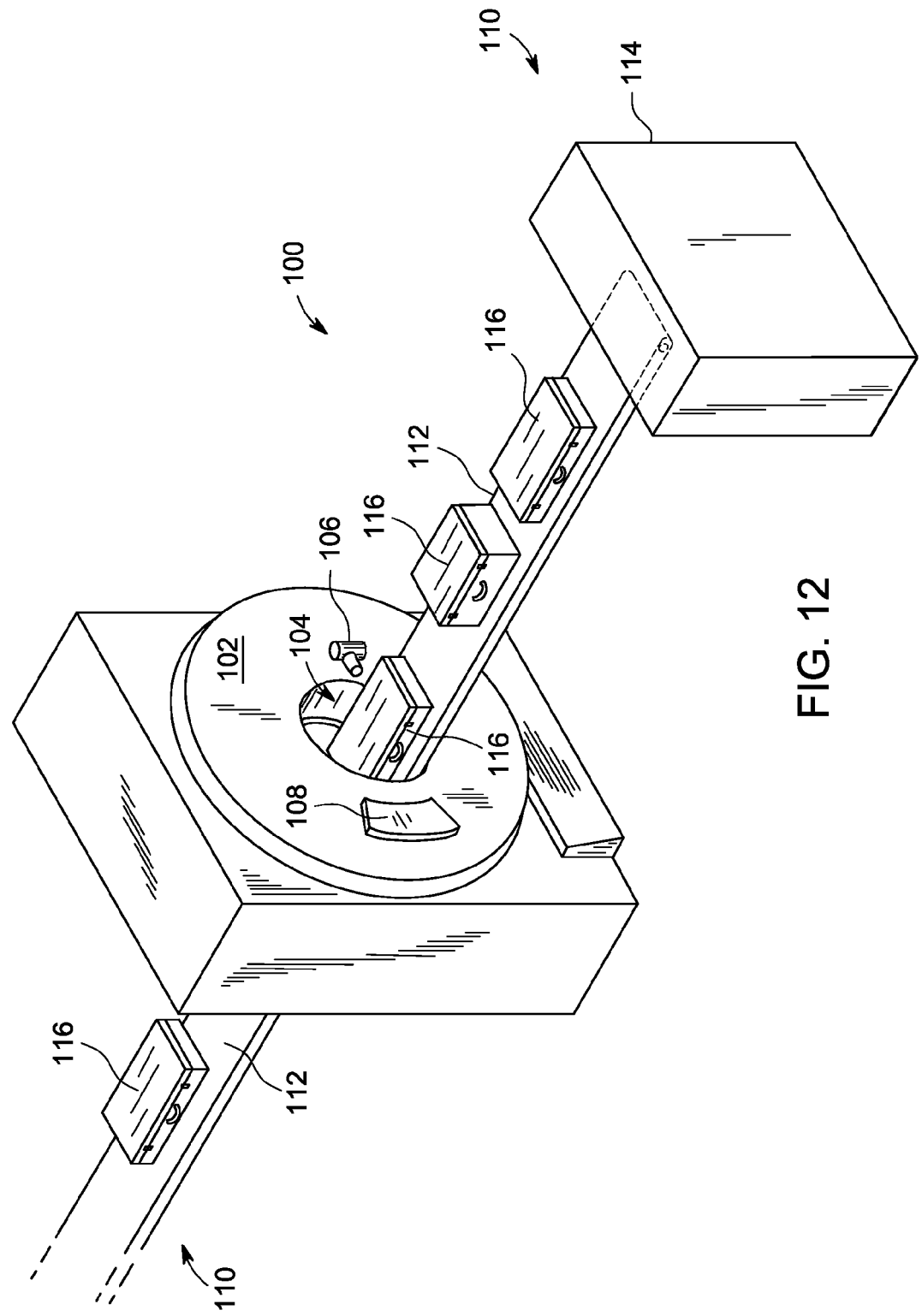
FIG. 12 is a pictorial view of a CT system for use with a non-invasive package inspection system.

Referring now to FIG. 12, a package/baggage inspection system 100 is shown that includes a rotatable gantry 102 having an opening 104 therein through which packages or pieces of baggage may pass. The rotatable gantry 102 houses a high frequency electromagnetic energy source 106 as well as a detector assembly 108 having detector modules 20 similar to that shown in FIGS. 4, 5, 11. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

According to an embodiment of the invention, incorporation of detector modules 20 (FIGS. 4, 5, 11) into the package/baggage inspection system 100 provides for decreased scanning time of packages 116. That is, detector modules 20 (FIGS. 4, 5, 11) allow for system 100 to scan a greater volume of the packages in a single revolution of gantry 102, as 256 slices can be acquired by detector modules 20. A more efficient scanning of packages 116 by package/baggage inspection system 100 is thus accomplished by way of detector modules 20 (FIGS. 4, 5, 11) being incorporated into the system 100.

Therefore, according to one embodiment of the invention, a CT system includes a rotatable gantry having an opening to receive an object to be scanned, an x-ray projection source positioned on the rotatable gantry that projects a cone beam of x-rays from a focal spot of the x-ray projection source toward the object, and a plurality of detector modules positioned on the rotatable gantry and configured to receive x-rays attenuated by the object. Each of the plurality of detector modules includes a module frame having a top surface thereon, a plurality of tileable sub-modules positioned on the top surface of the module frame and aligned along a Z-axis thereof so as to receive the x-rays attenuated by the object and convert the x-rays to digital signals, and an electronics board connected to the plurality of sub-modules to receive the digital signals therefrom. Each of the plurality of sub-modules on the detector module further includes an array of detector elements configured to receive x-rays attenuated through the object and convert the x-rays into analog electrical signals, an application specific integrated circuit (ASIC) electronics package electrically and mechanically coupled to the array of detector elements to receive the analog electrical signals and convert the analog electrical signals to digital signals, and a flex circuit connected to the ASIC electronics package to receive the digital signals therefrom and transfer the digital signals to the electronics board of the detector module.

According to another embodiment of the invention, a detector module for receiving x-rays attenuated by an object during a CT scan procedure includes a module frame, a plurality of tileable sub-modules positioned on the module frame to receive the x-rays attenuated by the object, and an electronics processing board secured to the module frame and electrically connected to the plurality of sub-modules to process signals received therefrom. Each of the plurality of sub-modules further includes an array of detector pixels configured to receive x-rays attenuated through the object and convert the x-rays into analog electrical signals, an application specific integrated circuit (ASIC) electronics package electrically and mechanically coupled to the array of detector pixels to receive the analog electrical signals and convert the analog electrical signals to digital numbers, and a digital flex circuit connected to the ASIC electronics package to receive the digital numbers therefrom and transfer the digital numbers to the electronics board of the detector module.

According to yet another embodiment of the invention, a detector module for receiving x-rays attenuated by an object during a CT scan procedure includes a module frame, a plurality of selectively addable sub-modules positioned on the module frame to receive the x-rays attenuated by the object, and an electronics processing board secured to the module frame and electrically connected to the plurality of sub-modules to process signals received therefrom. Each of the plurality of sub-modules includes a scintillator array having a plurality of scintillator pixels configured to receive x-rays attenuated through the object and generate a light output responsive thereto and a photodiode array optically coupled to the scintillator array and comprising a plurality of photodiodes each configured to detect the light output from the scintillator array and generate the analog electrical signals responsive thereto. Each of the plurality of sub-modules further includes an analog-to-digital (A/D) converter electrically and mechanically coupled to the array of detector elements to receive the analog electrical signals and convert the analog electrical signals to digital numbers, a substrate layer positioned on a back surface of the A/D converter opposite from the photodiode array to provide support to the sub-module, and a digital flex circuit connected to the A/D converter to receive the digital numbers therefrom and transfer the digital numbers to the electronics board of the detector module, the digital flex circuit including an interface portion thereon positioned between the A/D converter and the substrate layer to form an electrical and mechanical coupling with the A/D converter.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
    a rotatable gantry having an opening to receive an object to be scanned;
    an x-ray projection source positioned on the rotatable gantry that projects a cone beam of x-rays from a focal spot of the x-ray projection source toward the object; and
    a plurality of detector modules positioned on the rotatable gantry and configured to receive x-rays attenuated by the object, each of the plurality of detector modules comprising:
        a module frame having a top surface thereon;
        a plurality of tileable sub-modules positioned on the top surface of the module frame and aligned along a Z-axis thereof so as to receive the x-rays attenuated by the object and convert the x-rays to digital signals; and
        an electronics board connected to the plurality of sub-modules to receive the digital signals therefrom; and
    wherein each of the plurality of sub-modules comprises:
        an array of detector elements configured to receive x-rays attenuated through the object and convert the x-rays into analog electrical signals;
        an application specific integrated circuit (ASIC) electronics package electrically and mechanically coupled to the array of detector elements to receive the analog electrical signals and convert the analog electrical signals to digital signals; and
        a flex circuit connected to the ASIC electronics package to receive the digital signals therefrom and transfer the digital signals to the electronics board of the detector module.

2. The CT system of claim 1 wherein the array of detector elements comprises:
    a scintillator array having a plurality of scintillator pixels configured to receive x-rays attenuated through the object and generate a light output responsive thereto; and
    a photodiode array optically coupled to the scintillator array and comprising a plurality of photodiodes each configured to detect the light output from the scintillator array and generate the analog electrical signals responsive thereto.

3. The CT system of claim 1 wherein the ASIC electronics package comprises an input-output (I/O) interconnect system to electrically and mechanically couple the ASIC electronics package to the array of detector elements and to the flex circuit.

4. The CT system of claim 3 wherein the I/O interconnect system comprises a ball grid array (BGA) formed on each of a front and back surface of the ASIC electronics package.

5. The CT system of claim 1 wherein the ASIC electronics package comprises a plurality of individual ASIC dies.

6. The CT system of claim 1 wherein the flex circuit comprises one of a single-sided flex circuit extending out from one edge of the ASIC electronics package and a double-sided flex circuit extending out from each of a pair of opposing edges of the ASIC electronics package.

7. The CT system of claim 1 wherein the flex circuit comprises an interface configured to electrically and mechanically couple the flex circuit to the ASIC electronics package.

8. The CT system of claim 7 wherein each of the plurality of sub-modules further comprises an electrically insulating ASIC package substrate layer positioned on a back surface of the ASIC electronics package opposite from the array of detector elements, and wherein the interface of the flex circuit is positioned between the substrate layer and the ASIC electronics package.

9. The CT system of claim 8 wherein the flex circuit includes a bondable area configured to interface with the ASIC electronics package, the bondable area including a plurality of holes formed therein to thermally bond the ASIC electronics package to the ASIC package substrate layer.

10. The CT system of claim 1 wherein each of the plurality of tileable sub-modules is selectively addable to the module frame to vary an amount of coverage of the detector module along the Z-axis.

11. The CT system of claim 1 wherein the array of detector elements in each of the plurality of sub-modules comprises an array of controllable size, with the size of the array being determined so as to optimize cost, performance, yield, testing time scalability, and reliability.

12. The CT system of claim 1 wherein each of the plurality of detector modules is configured to acquire up to 512 image data slices during a single rotation of the x-ray source about the rotatable gantry.

13. A detector module for receiving x-rays attenuated by an object during a CT scan procedure, the detector module comprising:
a module frame;
a plurality of tileable sub-modules positioned on the module frame to receive the x-rays attenuated by the object; and
an electronics processing board secured to the module frame and electrically connected to the plurality of sub-modules to process signals received therefrom;
wherein each of the plurality of sub-modules comprises:
an array of detector pixels configured to receive x-rays attenuated through the object and convert the x-rays into analog electrical signals;
an application specific integrated circuit (ASIC) electronics package electrically and mechanically coupled to the array of detector pixels to receive the analog electrical signals and convert the analog electrical signals to digital numbers; and
a digital flex circuit connected to the ASIC electronics package to receive the digital numbers therefrom and transfer the digital numbers to the electronics board of the detector module.

14. The detector module of claim 13 wherein the array of detector pixels comprises:
a scintillator array having a plurality of scintillator pixels configured to receive x-rays attenuated through the object and generate a light output responsive thereto; and
a photodiode array optically coupled to the scintillator array and comprising a plurality of photodiodes each configured to detect the light output from the scintillator array and generate the analog electrical signals responsive thereto.

15. The detector module of claim 13 wherein the ASIC electronics package comprises an input-output (I/O) interconnect system to electrically and mechanically couple the ASIC electronics package to the array of detector pixels and to the flex circuit.

16. The detector module of claim 13 further comprising a substrate layer positioned on a back surface of the ASIC electronics package opposite from the array of detector pixels to provide support to the sub-module, the substrate layer being formed of an electrically insulating material.

17. The detector module of claim 13 wherein each of the plurality of tileable sub-modules is selectively addable to and removable from the module frame, such that a number of sub-modules included in the detector module is controllable so as to vary an amount of coverage of the detector module along the Z-axis.

18. A detector module for receiving x-rays attenuated by an object during a CT scan procedure, the detector module comprising:
a module frame;
a plurality of selectively addable sub-modules positioned on the module frame to receive the x-rays attenuated by the object; and
an electronics processing board secured to the module frame and electrically connected to the plurality of sub-modules to process signals received therefrom;
wherein each of the plurality of sub-modules comprises:
a scintillator array having a plurality of scintillator pixels configured to receive x-rays attenuated through the object and generate a light output responsive thereto;
a photodiode array optically coupled to the scintillator array and comprising a plurality of photodiodes each configured to detect the light output from the scintillator array and generate analog electrical signals responsive thereto;
an analog-to-digital (A/D) converter electrically and mechanically coupled to the photodiode array to receive the analog electrical signals and convert the analog electrical signals to digital numbers;
a substrate layer positioned on a back surface of the A/D converter opposite from the photodiode array to provide support to the sub-module; and
a digital flex circuit connected to the A/D converter to receive the digital numbers therefrom and transfer the digital numbers to the electronics board of the detector module, the digital flex circuit including an interface portion thereon positioned between the A/D converter and the substrate layer to form an electrical and mechanical coupling with the A/D converter.

19. The detector module of claim 18 wherein the module frame is configured to arrange the plurality of selectively addable sub-modules positioned thereon in an approximated curve formed in a circular arc not following the arc of the x-rays or a stepped configuration with a plurality of angled facets thereon.

20. The detector module of claim 18 wherein the A/D converter comprises an input-output (I/O) interconnect system to electrically and mechanically couple the A/D converter to the photodiode array and to the flex circuit.

21. The detector module of claim 18 wherein the A/D converter comprises a pair of ASIC electronics packages, with each of the ASIC electronics packages including one or more ASIC dies therein.

22. The detector module of claim 18 wherein each of the plurality of sub-modules is selectively addable to and removable from the module frame, such that a number of sub-modules included in the detector module is controllable so as to vary an amount of coverage of the detector module along the Z-axis.

* * * * *